United States Patent [19]

Jennings et al.

[11] 4,129,587

[45] Dec. 12, 1978

[54] DIMERIZATION PROCESS

[75] Inventors: James R. Jennings; Dipankar Sen, both of Runcorn, England

[73] Assignee: Imperial Chemical Industries Limited, London, England

[21] Appl. No.: 854,491

[22] Filed: Nov. 23, 1977

[30] Foreign Application Priority Data

Nov. 24, 1976 [GB] United Kingdom ............... 48959/76

[51] Int. Cl.² .................. C07C 120/00; C07C 121/20
[52] U.S. Cl. ............................................. 260/465.8 D
[58] Field of Search ................................. 260/465.8 D

[56] References Cited

U.S. PATENT DOCUMENTS

| 3,567,759 | 3/1971 | Tullio | 260/465.8 D |
| 3,644,473 | 2/1972 | Onsager | 260/465.8 D |
| 3,732,287 | 5/1973 | Himmele et al. | 260/476 R |

FOREIGN PATENT DOCUMENTS

| 1385883 | 12/1964 | France | 260/465.8 D |
| 45-35288 | 11/1970 | Japan | 260/465.8 D |
| 49-28491 | 7/1974 | Japan | 260/465.8 D |
| 1003656 | 9/1965 | United Kingdom. | |
| 1154275 | 6/1969 | United Kingdom | 260/465.8 D |
| 1177182 | 1/1970 | United Kingdom | 260/465.8 D |

OTHER PUBLICATIONS

Muller, et al., Ind. Chem. Belgium (1967) vol. 38, Part III, pp. 38–41.

*Primary Examiner*—Joseph Paul Brust
*Attorney, Agent, or Firm*—Cushman, Darby & Cushman

[57] ABSTRACT

Process for the dimerisation of acrylonitrile (ACN) to predominantly linear $C_6$ dimers using organic phosphinites or phosphonites as catalyst in the presence of a proton-donating solvent and, optionally, a hydrocarbon co-solvent, the ACN and solvent(s) being substantially dry, and a small amount of a compound of a metal of Group IVA to VIIA, VIII or IB to VB being added to the reaction mixture to reduce the amount of polymeric by-product.

8 Claims, No Drawings

DIMERIZATION PROCESS

This invention relates to a dimerisation process and, especially, to a process for the dimerisation of acrylonitrile to linear $C_6$ dinitriles.

In our copending British Patent application No. 45324/75 and our allowed U.S. Application Ser. No. 736,498 filed Oct. 28, 1976, we describe a process for the dimerisation of acrylonitrile to predominantly straight-chain $C_6$ dimers, which comprises contacting the acrylonitrile with an organic phosphorus (III) compound having at least one hydrocarbyl and at least one alkoxy or cycloalkoxy group attached to the phosphorus atom or atoms, the acrylonitrile being dissolved in an inert organic solvent capable of donating protons, and the acrylonitrile and solvent being substantially dry.

By the use of this process, predominantly linear $C_6$ dimers of acrylonitrile, especially the 1,4-dicyanobutenes, may be prepared in good yield, the desired products being readily separated from the reaction mixture by fractional distillation or solvent extraction.

A modification of the above process, described in our cognate copending British Patent application No. 52887/75 and also described in our allowed U.S. Application Ser. No. 736,498 filed Oct. 28, 1976, involves the addition of a non-hydroxylic co-solvent, preferably a hydrocarbon, which gives rise to a reduction in the proportion of oligomeric and polymeric by-products.

We have now found that the proportion of oligomeric and/or polymeric by-products may be reduced still further by the addition of small quantities of certain metal compounds.

According to the present invention, we provide a process for the dimerisation of acrylonitrile in which the acrylonitrile is contacted with an organic phosphorus (III) compound having at least one alkoxy or cycloalkoxy group and at least one hydrocarbyl group attached to the phosphorus atom or atoms, the acrylonitrile being dissolved in an organic solvent capable of donating protons, optionally with an inert non-hydroxylic co-solvent, the acrylonitrile and solvent or solvents being substantially dry, characterised in that an effective amount of an anhydrous metal compound capable of reducing the proportion of polymeric by-products is added to the reaction mixture, the metal being selected from Groups IVA to VIIA, VIII and IB to VB of the Periodic Table of Elements.

By polymeric by-products we mean polymeric solids and/or oils e.g. the hexamer of acrylonitrile, 1,1′ 2,2′tetracyanoethyl 1,4 dicyanobutene-2, which are commonly co-produced with the desired dimeric products.

(All references to the Periodic Table of the Elements are to the version printed inside the back cover of "Advanced Inorganic Chemistry" by F R Cotton and G Wilkinson, 3rd Edition, Interscience Publishers, 1972).

Since the reaction mixture must be substantially dry the metal compound must be in the anhydrous state. It is also preferred that the compound is non-hygroscopic for ease of handling, although this property may not prevent its satisfactory performance in our process. For example, although many metal halides in the anhydrous state, e.g. $ZnCl_2$, $NiCl_2$ and $FeCl_3$ are hygroscopic, they are effective in our process and may be used effectively when handled using inert atmosphere techniques.

Although a large number of compounds of metals from the above mentioned Groups of the Periodic Table are effective in the practice of the present invention, it will be appreciated that some compounds are more effective than others, that some will have little or no effect and a few may have a deleterious effect. However, the following guidelines will enable the skilled worker to select those compounds which have the desired effect, and furthermore we provide at the end of the experimental section a simple test by which the effectiveness of any particular metal compound may be quickly assessed.

The metal of the compound is preferably in an "intermediate" oxidation state. In this context, a metal is considered to be in an "intermediate" oxidation state if it remains in the same state in the reaction medium, i.e. it does not tend to reduce or oxidise any component of the reaction mixture. Examples of so-called "intermediate" oxidation states of some suitable metals include Zn(II), Ni(II), Ti(III), V(III) Cr(III), Mn(II), Fe(II), Fe(III), Al(III), Ge(IV), Rh(I), Pt(II), Cu(I), Cu(II), Ag(I), Cd(II) and Hg(II).

Metal compounds in high oxidation states, e.g. Cr(VI) Mn(VII), in $Na_2Cr_2O_7$ or $KMnO_4$ may be at least partially reduced by the reaction medium to a lower oxidation state and hence be effective in reducing polymeric by-products. Metal compounds which alcoholise to acidic products, e.g. $AlCl_3$ and $TiCl_4$, should be avoided, since whereas some of these may well reduce polymer/hexamer formation, the acidic products will tend to react with the acrylonitrile and/or catalyst and hence reduce the overall yield of dimeric product, or especially the conversion of acrylonitrile to dimers.

It is preferred that the metal compound should have some solubility in the reaction media; but it is not necessary for it to be completely soluble. For example, $ZnCl_2$ and $NiCl_2$ are completely soluble in the reaction media at the required concentration; and $TiCl_3$, $VCl_3$, $CrCl_3$. 3THF and $PtCl_2$ have sufficient solubility to be effective.

When the metal compound is a co-ordination complex, suitable ligands include tertiary amines, ethers, nitriles, phosphines, phosphinites, phosphonites, phosphite, tertiary arsines, organic sulphides and chelating ligands including acylacetones, α-hydroxyoximes and diphosphines.

However, simple salts may also be used; for example, halides, (especially chlorides), sulphates and carboxylates.

Especially convenient metal compounds are the chlorides of zinc, nickel and cobalt, and the acetylacetonates of zinc, nickel, gallium and aluminium.

The effective concentration of metal compound in the reaction mixture will depend on the precise metal compound chosen; but can readily be determined by the afore-mentioned sorting test. However, concentrations will generally be in the range 5 to 1000 ppm by weight calculated on the total reaction medium. Concentrations outside this range may be used; but concentration < 5 ppm do not normally give rise to worthwhile reductions in polymer formation and concentrations > 1000 ppm tend to be wasteful in respect of the metal compound and may unduly reduce the level of dimerisation. For many metal compounds there appears to be a maximum effective concentration above which further additions of metal compound has no appreciable effect on the production of polymeric products.

The optimum concentration of metal compound is also dependent upon catalyst concentration, in that the metal compound concentration should not normally exceed about 10% of the catalyst concentration. Preferably, the metal compound concentration is from 0.5 to 5% of the catalyst concentration.

The metal compound may be added as a solid or as a solution in a solvent which is compatible with the reaction mixture. The metal compound may be added before or after the other components; but it is preferred to add it before the phosphorus (III) compound is added so that the metal compound is present in the reaction medium before dimerisation can commence.

The most important advantage obtained by the addition of our metal compounds is the reduction of the amount of polymeric (e.g. hexamer) by-product. However, many of the compounds also give rise to an increased yield of 1,4-dicyanobutene.

As stated in our afore-mentioned copending patent applications, the presence of a proton-donating solvent is essential to our process, as in the absence of solvent rapid polymerisation of the acrylonitrile occurs. It is also preferable that the proton-donating solvent and any co-solvent are substantially unreactive to acrylonitrile and the reaction products with respect to addition or reaction with the unsaturated linkage of the acrylonitrile under the reaction conditions. It is also essential that the solvent(s) must not react with the phosphorus compound catalyst to form an inactive species at least at such a rate as to seriously impair the catalysis of the dimerisation reaction.

Further, it is preferred that one or both of said solvents has a boiling point higher than that of acrylonitrile and is capable of rapid phase separation with respect to the dimeric reaction products, as described in our British Patent application No. 19108/76 and our allowed U.S. Application Ser. No. 793,272 filed May 3, 1977. This enables unreacted acrylonitrile to be distilled from the reacted mixture leaving the dimeric products and high boiling solvent as a readily separable two-phase mixture.

Preferably, the proton-donating solvent is a hydroxylic solvent, such as an alcohol, provided that it is unreactive as defined above. If the proton-donating solvent is the sole solvent it must be "high-boiling". Suitable high boiling proton-donating solvents include decanol, nonanol, octanol, iso-octanol, 2 ethylhexanol, heptanol, phenyldimethyl carbinol and isomers and mixtures thereof. There may be some reaction between ACN and the alcohol, the effect being most pronounced with primary alcohols. For this reason tertiary alcohols such as phenyldimethyl carbinol and t-butanol are preferred. However, the advantages of catalyst and product separation may be sufficiently great to allow the use of primary alcohols. When a high-boiling co-solvent is used, suitable proton-donating solvents also include t-butyl alcohol and iso-propanol.

The non-hydroxylic co-solvent is preferably a hydrocarbon. Suitable high-boiling co-solvents include decalin, petroleum ether (b.pt. > 110° C.), tetralin and kerosene.

When the proton-donating solvent is high-boiling, the co-solvent need not be high-boiling; in this case suitable hydrocarbon co-solvents include hexane, cyclohexane and benzene.

When present, the proportion of co-solvent in the reaction mixture may be varied over the wide limits. In general the ratio of proton-donating solvent to co-solvent is in the range 1:9 to 9:1, but ratios outside these limits may be used. Conveniently the said ratio is in the range 1:2 to 2:1, for example about 1:1. However, the final choice of ratio will depend on how it is desired to run the process.

For example, when t-butanol is used with isopropyl diphenyl phosphinite, solvent/co-solvent ratios in the range 1/1 to 1/5 are preferred. However, when isopropanol is used with isopropyl ethyl (phenyl) phosphinite, ratios in the range 1/3 to 1/7 are preferred; and when isopropyl diethylphosphinite is used preferred ratios are in the range 1/5 to 1/20. The above ratios are by volume.

Changes in the ratio of proton-donating solvent/co-solvent are generally reflected by changes in the amount of polymers formed and changes in the reaction rate. These changes in reaction parameters are often dependant upon the actual catalyst and solvent system chosen. For example, addition of toluene to a dimerisation system comprising acrylonitrile, tertiary butanol and isopropyldiphenylphosphinite results in a reduction in the production of polymers, but also in a reduction in the rate of reaction. The presence of a co-solvent also allows higher reaction temperatures to be used and, in some cases, has a stabilising effect on the phosphorus (III) compounds used as catalysts.

The ratio of linear to branched dimers is dependent on the solvent/co-solvent ratio in some instances. It is sometimes found that, as the proportion of proton-donating solvent decreases, the proportion of linear dimer increases and vice-versa.

The concentration of acrylonitrile in the solvent mixture generally should range from 5 to 75% by volume. The concentration of acrylonitrile is kept as high as possible in order to optimise throughput. However, in order to achieve maximum catalyst separation from the dimeric products, the concentration of solvent should be kept as high as possible. Generally, concentrations in the range 10 to 50% by volume form a convenient compromise.

As described in our aforementioned co-pending application, suitable organic phosphorus (III) compounds include those of general formulae:

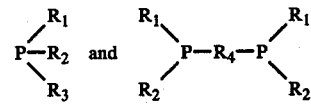

where $R_1$ is a hydrocarbyl group, $R_2$ is an alkoxy or cycloalkoxy group, $R_3$ is hydrocarbyl, alkoxy or cycloalkoxy group or other monovalent radical, and $R_4$ is a divalent hydrocarbyl hydrocarbyloxy or other difunctional group. It is also possible that one or more groups $R_1$ to $R_3$ may form part of one or more ring systems.

The hydrocarbyl groups may be aryl, alkyl, alkaryl, aralkyl or cycloalkyl.

The alkoxy or cyclo alkoxy group or groups may contain similar substituents and may also contain aryl substituents. Examples of suitable alkoxy groups include methoxy, ethoxy and isopropoxy; but aryloxy groups are not suitable.

High proportions of straight-chain dimers are obtained where each hydrocarbyl group is aryl, in the case where either 1 or 2 hydrocarbyl groups are present in the phosphorus (III) compound. High reaction rates are obtained where one or both of the hydrocarbyl groups is alkyl in cases where two hydrocarbyl groups are present; but these high reaction rates may be accompanied by somewhat lower proportions of straight-chain dimers than where both hydrocarbyl groups are simple aryl. The hydrocarbyl groups may contain substituents, suitable substituent groups being halogen, cyanide, alkyl and alkoxy. High rates may also be achieved by the use of substituted aryl groups, for example p-methoxyphenyl. The alkoxy or cycloalkoxy group or groups may contain similar substituents and may also contain aryl substituents. Examples of suitable alkoxy groups include methoxy, ethoxy, benzyloxy and isopropoxy. Suitable examples of divalent groups $R_4$ include alkylene, polyalkylene and phenylene and poly phenylene groups, alkylene dioxy and polyalkylene dioxy groups.

Groups $R_1$ to $R_4$ may also be part of a polymeric backbone, for example polystyrene or polyvinyl alcohol, or be linked to an inorganic support, for example silica or alumina.

Provided that the groups $R_1$ to $R_4$ do not give rise to undesirable steric effects there is no finite limit on the number of carbon atoms they may contain. However, they will commonly contain from 1 to 10 carbon atoms.

It will be appreciated from the above that in the phosphorus (III) compounds which are useful in our invention each phosphorus atom must have at least one hydrocarbyl and one alkoxy group attached to it, but must not bear only hydrocarbyl or only alkoxy groups. Our preferred phosphorus (III) compounds are thus phosphinites or phosphonites.

Examples of suitable phosphorus (III) compounds include diethyl phenylphosphonite, dimethyl phenylphosphonite; dimethyl p-methylphenylphosphonite, diethyl p-methylphenylphosphonite, isopropyl bis p-methylphenylphosphinite, methyl diphenylphosphinite, isopropyl diphenylhosphinite, ethyl phenylethylphosphinite, ethyl diphenylphosphinite, cyclohexyl diphenylphosphinite, diethyl p-tolylphosphonite, 2-ethylhexyl diphenylphosphinite, bis(2-ethylhexyl) phenylphosphonite, di(isopropyl) phenylphosphonite, di(neopentyl) phenylphosphonite, 2-octyl diphenylphosphinite, bis(3,5,5-trimethylhexyl) phenylphosphonite, 2-methylcyclohexyl diphenylphosphinite, 3,5,5-trimethylhexyl diphenylphosphinite, sec.butyl diphenylphosphinite, cyclohexyl diphenylphosphinite, benzyl diphenylphosphinite, isopropyl bis p-methoxyphenylphosphinite, isopropyl p-methoxyphenyl (phenyl)phosphinite, isopropyl bis p-dimethylaminophenylphosphinite, $Ph_2PO(CH_2)_4OPPh_2$, $Ph_2POCH(-CH_2)_2CHOPPh_2$ and
        |                     |
        Me                    Me

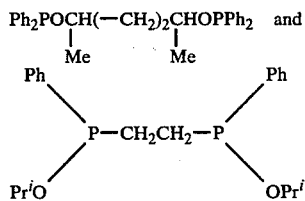

We have found that phosphinites such as $Ph_2P(OisoPr)$ with branched alkyl groups are especially useful in our process, as they partition very favourably with respect to many suitable high boiling solvents.

The concentration of the phosphorus compound in the reactant mixture may be varied over a wide range, for example, from 0.005, commonly 0.01 to 5% by volume, calculated on the volume of liquid reactants; but preferably the concentration is in the range 0.01 to 1% by volume.

The reaction temperature is commonly in the range 0° to 200° C., because the presence of the hydrocarbon solvent tends to inhibit the polymerisation of the acrylonitrile and dimeric products. Preferably, the reaction temperature is in the range 60° to 150° C.

An essential feature of the present invention is that the reaction must be conducted in the substantial absence of water. Thus, the acrylonitrile and solvent must be dried before use, otherwise the reaction may be completely inhibited. In particular the acrylonitrile, which commonly contains as much as 4000 ppm of water, even after distillation, must be rigorously dried. It is also noted that hydroquinone stabilisers, which are present in the acrylonitrile as supplied, should be removed. For example, if the reactants contain 300 ppm of water, reaction is virtually inhibited at a concentration of the phosphorus compound of 0.5% by volume; but at water concentrations of 50 ppm or lower reaction takes place readily. Any suitable drying technique may be used, provided that the final water level is sufficiently low. For example, acrylonitrile and hydroxylic solvents may be dried by being contacted with calcium hydride or a 3A or 4A molecular sieve. It is also possible to remove substantially all the water by azeotropic distillation. Similarly it is preferred that the metal compound is in the anhydrous state. Further, we find that reaction rates are somewhat higher and catalyst lifetimes longer when the process is operated under an inert atmosphere such as dry nitrogen gas. This inert atmosphere not only reduces contamination by water but any adverse reactions caused by the presence of oxygen. The above findings contrast strongly with the teaching of the prior art which makes no mention of removal of water and/or hydroquinone stabilisers, and in many instances advocates the addition of water and stabilisers, such as hydroquinone, to the reaction mixture.

The reaction may be carried out batchwise or continuously. In the latter case it may be convenient to support the catalyst compound or to use a polymeric trivalent phosphorus compound to enable the reaction to be carried out in the liquid phase using a heterogeneous catalyst.

The dimeric products of our invention are predominantly linear $C_6$ dinitriles, especially the 1,4-dicyanobutenes. Selectivities > 90% may be readily obtained and selectivities as high as 98% have been obtained using our most advantageous catalysts. In each case the selectivity is calculated on the total dimeric product.

When reaction is complete, the unreacted acrylonitrile and any volatile solvent which may be present is removed by fractional distillation, leaving the dimeric products, plus any high boiling solvent or solvents, when present. In this latter case, the mixture is allowed to separate into two phases and the upper, or solvent, phase is separated, together with an appropriate proportion of the phosphorus (III) compounds.

It will be appreciated that by using the above process, the separations achieved allow recycle of unreacted acrylonitrile and catalyst solution, requiring only make-up of the components consumed.

The invention will be illustrated by the following Examples.

General

Acrylonitrile, isopropanol and t-butanol used in the following Examples were dried by adding calcium hydride powder to them and allowing them to stand overnight. The liquid was then decanted on to fresh calcium hydride powder and refluxed for 30 minutes. After this time, the liquid was distilled from the calcium hydride into a vessel containing 4A molecular sieve for storage until required. Toluene was dried by refluxing it in the presence of sodium/potassium alloy and benzophenone until the blue/violet ketyl formed. The toluene was then distilled into a vessel containing 4A molecular sieve for storage until required.

In each case the final water level of the dried solvent was about 15 ppm by volume, as determined by the Karl Fisher titration procedure.

Metal halides used in Examples 1, 2, 9 and 31 were dried by refluxing with $SOCl_2$, so that any water reacted to form gaseous $SO_2$ and hydrochloric acid. The halide was collected by filtration and dried under nitrogen as described by A. R. Pray in "Inorganic Synthesis" Vol IV, 1957 pp 153-156. Other halides were available in the anhydrous state.

In all Examples "% conversion" indicates the % by weight of acrylonitrile (ACN) converted to total dimeric and polymeric products; the "% yield" of a product is the weight of that product calculated as a % of the weight of ACN converted.

All analyses of dimeric products were made by gas/-liquid chromatography (g.l.c.).

The phosphorus (III) compounds used in the Examples are either commercially available or were prepared using methods given in "Organo-Phosphorus Compounds", Kosolapoff and Maier published by Wiley 1972, Vol 4, Chapters 10 and 11.

EXAMPLE 1

Two portions each of acrylonitrile (3 ml) isopropanol (1 ml) and toluene (3 ml) dried as described above, were mixed separately under an atmosphere of nitrogen. $ZnCl_2$ (5.4 mg ≡ 386ppm) was added to one mixture, both were heated to 60° C. and isopropyl bis p-methoxyphenylphosphinite (150 mg) was added to each. The mixtures were maintained at this temperature for 3 hours. At the end of this time, water was added to terminate the reaction and the solid polymeric products filtered (reported as "hexamer"). Solvents and unreacted acrylonitrile were removed by vacuum distillation. The residue was weighed and analysed by g.l.c. using adiponitrile as internal standard. The results are given in Table 1 below.

TABLE 1

|  | % Conversion | % 1-4 DCB | % Hexamer |
|---|---|---|---|
| Example 1 | 66 | 89 | 0.08 |
| Blank | 75 | 84 | 1.34 |

Although total conversion was reduced slightly the hexamer by-product was reduced considerably with some improvement in selectivity to 1-4 dicyanobutene (1-4DCB).

EXAMPLE 2

The procedure of Example 1 was repeated using $CoCl_2$ (214 ppm) in place of $ZnCl_2$. Results are given in Table 2 below.

TABLE 2

|  | % Conversion | % 1-4 DCB | % Hexamer |
|---|---|---|---|
| Example 2 | 74.3 | 85.7 | 0.6 |
| Blank | 76.7 | 81.4 | 1.7 |

EXAMPLES 3-8

Portions of acrylonitrile (10 ml) isopropanol (5 ml) and toluene (10 ml) were mixed separately. One was kept as a blank and various metal acetylacetonates (200 ppm) were added separately to the other mixtures. All the mixtures were then heated to 60° C., isopropyl diphenylphosphinite (250 mg) added to each and the mixtures maintained at 60° C. for 3 hours. Reaction was terminated and product worked up as described for Example 1. Results are given in Table 3 below.

TABLE 3

| Example | Acetylacetonate | % Conversion | % 1-4 DCB | % Hexamer |
|---|---|---|---|---|
| 3 | Zn(II) | 37.5 | 85 | 2.5 |
| 4 | Ga(II) | 15 | 85 | <1 |
| 5 | Al(III) | 33 | 83 | 3.5 |
| 6 | Ge(IV) | 33 | 79 | 5 |
| 7 | Mn(III) | 47 | 67 | 12 |
|  | Blank | 47 | 64.5 | 13.5 |

When the procedure was repeated with thorium acetylacetonate (i.e. a metal of Group IIIA), hexamer yield was increased and the 1-4 DCB yield was reduced.

EXAMPLE 9

The general procedure of Examples 3-8 was followed, using acrylonitrile (10 ml), t-butanol (10 ml) and toluene (10 ml). $NiCl_2$ (113 ppm) was used as the metal compound and reaction was allowed to proceed for 16 hours at 22° C. The results are given in Table 4.

TABLE 4

|  | % Conversion | % 1-4 DCB | % Hexamer |
|---|---|---|---|
| Example 9 | 27.6 | 87.8 | 0.9 |
| Blank | 27.9 | 78.2 | 4.1 |

EXAMPLE 10

The procedure of Example 9 was repeated with only 5 ml of t-butanol and nickel (II) acetylacetonate (264 ppm). The results are given in Table 5.

TABLE 5

|  | % Conversion | % 1-4 DCB | % Hexamer |
|---|---|---|---|
| Example 10 | 37.3 | 82.1 | 6.5 |
| Blank | 46.4 | 65.0 | 14.5 |

EXAMPLES 11-32

A stock solution was prepared by mixing equal volumes of acrylonitrile, t-butanol and toluene, each dried as described above. The mixture was stored under nitrogen until required. Pairs of aliquot portions (75 ml) were transferred under nitrogen to reaction vessels, a measured amount of a metal complex being added to one portion, the other being used as a blank experiment. The mixtures were heated to reaction temperature and 0.5 g of isopropyl diphenylphosphinite added as catalyst. The mixtures were retained at this temperature for a given time, after which the reaction was terminated and reaction mixture worked up as described under Example 1. The results are given in Table 6.

It will be seen from Table 6 that the addition of small amounts of a large variety of metal compounds gives rise to a marked reduction in "hexamer" formation. Although this is often accompanied by some reduction in overall conversion, the advantage of reduction of hexamer plus some increase in yield of DCB far outweighs any reduction in conversion.

The comparative tests C1–C5 demonstrate the following effects:

C1; Metal of Group 1A — increase in hexamer
C2; Metal in unusually high oxidation state.
C3; Metal in low oxidation state.
C5; Metal in high oxidation state giving very low conversion.

TABLE 6

| Ex No. | Metal Compound | Wt ppm | % Yield DCB Sample | % Yield DCB Blank | % Yield "Hexamer" Sample | % Yield "Hexamer" Blank | % Conversion Sample | % Conversion Blank | Temp °C | Time Hrs |
|---|---|---|---|---|---|---|---|---|---|---|
| 11 | $VCl_3$ | 573 | 92 | 69 | <1 | 8 | 16 | 35 | 60 | 18.5 |
| 12 | $CdCl_2$ | 360 | 87 | 72 | <1 | 8 | 19 | 31 | 22 | 18.5 |
| 13 | $PtCl_2$ | 333 | 90 | 68 | <1 | 8 | 22 | 27 | 22 | 24 |
| 14 | $PtCl_2$ | 373 | 94 | 63 | 1 | 12 | 31 | 57 | 22 | 91 |
| 15 | HgCl | 467 | 85 | 64 | 2 | 11 | 16 | 29 | 22 | 17 |
| 16 | AgCl | 333 | 88 | 68 | <1 | 8 | 28 | 27 | 22 | 24 |
| 17 | Diphos $PtBr_2$ | 400 | 89 | 80 | 1 | 6 | 50 | 60 | 22 | 65 |
| 18 | Diphos $Ni\ I_2$ | 200 | 92 | 86 | <1 | 3 | 24 | 24 | 60 | 5 |
| 19 | $(Ph_3P)_2NiI_2$ | 307 | 93 | 86 | <1 | 3 | 21 | 24 | 60 | 5 |
| 20 | $(Ph_3P)_2CoBr_2$ | 267 | 81 | 69 | 3 | 7 | 25 | 26 | 5 | 60 |
| 21 | Co(II)Salen | 200 | 88 | 30 | 3 | 6 | 53 | 53 | 22 | 65 |
| 22 | $(PhCN)_2PdCl_2$ | 200 | 81 | 72 | <1 | 5 | 23 | 28 | 60 | 17 |
| 23 | $CrCl_3.8THF$ | 147 | 77 | 69 | <1 | 7 | 20 | 26 | 5 | 60 |
| 24 | $[Rh(Co)_2Cl]_2$ | 333 | 86 | 77 | <1 | 3 | 7 | 8 | 22 | 5 |
| 25 | " | 400 | 83 | 71 | 2 | 9 | 13 | 19 | 60 | 3 |
| 26 | $(Ph_2PoPr)CuCl$ | 333 | 88 | 78 | <1 | 5 | 40 | 40 | 22 | 19 |
| 27 | $(Ph_2POPr)_2NiCl_2$ | 333 | 82 | 62 | <1 | 12 | 18 | 21 | Reflux | 2.5 |
| 28 | $(Ph_2POPr)AgCl$ | 333 | 70 | 62 | <1 | 7 | 15 | 12 | 60 | 2.75 |
| 29 | Co(II)Salen | 267 | 88 | 86 | 1 | 3 | 24 | 24 | 60 | 5 |
| 30 | $CuSO_4$ | 173 | 89 | 73 | 1 | 7 | 23 | 30 | 22 | 17 |
| 31 | $AlCl_3$ | 253 | 89 | 73 | 1 | 7 | 11 | 30 | 22 | 17 |
| 32 | $SnCl_2$ | 160 | 80 | 73 | 2 | 7 | 27 | 30 | 22 | 17 |
| Comparative Tests | | | | | | | | | | |
| C1 | KI | 333 | 45 | 78 | 17 | 2 | 8 | 7 | 22 | 3.5 |
| C2 | $(Ph_3P)_2ReH_7$ | 533 | 73 | 80 | 3 | 6 | 35 | 55 | 22 | 65 |
| C3 | $CpFe(CO)_2I$ | 80 | 9 | 45 | 20 | 18 | 61 | 70 | 60 | 65 |
| C4 | $Ru_3(CO)_{12}$ | 267 | 81 | 79 | 4 | 7 | 28 | 23 | 22 | 24 |
| C5 | $KMnO_4$ | 133 | 80 | 56 | <1 | 10 | 10 | 69 | 22 | 72 |

Notes:
"Diphos" =bisdiphenylphosphinoethane
Cp =cyclopentadienyl
THF =tetrahydrofuran
"Hexamer" =solid and oily oligomeric products
DCB =1,4-dicyanobutanes
Pr =propyl
Ph =phenyl
Salen =N,N'-ethylene bis)salicylideneiminato)

EXAMPLE 33

The general procedure of Examples 11–32 was followed, using $TiCl_3$ (400 ppm) as metal compound at a reaction temperature of 60° C. for 18 hours. Results are given in Table 7.

TABLE 7

| | % Conversion | % 1-4 DCB | % Hexamer |
|---|---|---|---|
| Example 33 | 22 | 88 | <1 |
| Blank | 30 | 78 | 8 |

The following procedure provides a convenient rough "sorting test" by which one may assess the potential effectiveness of any metal compound falling within our definition.

Two aliquot portions (30 ml) of a stock solution prepared as described under Examples 11–32 are transferred to reaction flasks under an atmosphere of nitrogen. Then 5 mg of the metal compound to be tested is added to one portion, both are heated to 60° C. and isopropyl diphenylphosphinite (200 mg) is added to each. Each reaction mixture is retained at 60° C. for 3 hours, at the end of which time the reaction is terminated by the addition of water. The effectiveness of the compound under test may be assessed by determining the amount of insoluble hexamer in each flask. To be effective the amount of hexamer must be less in the flask to which the metal compound was added. The relative amounts of hexamer in sample and blank may often be estimated visually; but they may be readily determined quantitatively by filtration to remove the hexamer which thenthen be washed, dried and weighed. The precise effect of the addition of the metal compound may, of course be determined by g.l.c. analysis of the residue as previously described.

What we claim is:

1. A process for the dimerisation of acrylonitrile to predominantly 1,4-dicyanobutenes, in which the acrylonitrile is contacted with an organic phosphorus (III) compound having the formula

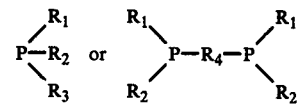

where $R_1$ is a hydrocarbyl group, $R_2$ is an alkoxy or cycloalkoxy group, $R_3$ is a hydrocarbyl, alkoxy or cycloalkoxy group and $R_4$ is a divalent hydrocarbyl or hydrocarbyloxy group, each hydrocarbyl or hydrocarbyloxy group having from 1 to 10 carbon atoms and being unsubstituted or substituted by halogen, cyanide or alkyl groups, at a temperature from 0° to 120° C., the acrylonitrile being dissolved in an organic solvent capable of donating protons, optionally with an inert non-hydroxylic co-solvent, the concentrations of acrylonitrole and said phosphorus (III) compound being in the ranges 5 to 75% and 0.01 to 5% by volume, respectively, and the acrylonitrile and solvent or solvents being substantially dry, characterised in that a polymeric by-product reducing amount of an anhydrous metal compound capable of reducing the proportion of polymeric by-products is added to the reaction mixture, the metal being selected from Group IVA to VIIA, VIII and IB to VB of the Periodic Table of Elements.

2. A process as claimed in claim 1, in which the concentration of the metal compound in the reaction mixture is between 5 and 1000 ppm.

3. A process as claimed in claim 1 in which the concentration of metal compound is from 0.5 to 5% of the concentration of phosphorus (III) compound.

4. A process as claimed in claim 1 in which the metal compound is a co-ordination complex.

5. A process as claimed in claim 1 in which the metal compound is a halide, a sulphate or a carboxylate.

6. A process as claimed in claim 4 in which the metal compound is an acetylacetonate of zinc, nickel, aluminium or gallium.

7. A process as claimed in claim 5 in which the metal compound is zinc, nickel or cobalt dichloride.

8. A process as claimed in claim 1 in which the metal compound is added to the reaction mixture before it is contacted with the phosphorus (III) compound.